United States Patent [19]

Grollier et al.

[11] Patent Number: 4,601,726

[45] Date of Patent: Jul. 22, 1986

[54] DYE COMPOSITION FOR THE DIRECT DYEING OF KERATINIC FIBRES, CONTAINING AT LEAST ONE N-SUBSTITUTED COSOLUBILIZED 2-NITROPARAPHENYLENEDIAMINE AND CORRESPONDING PROCESSES FOR DYEING KERATINIC FIBRES

[75] Inventors: Jean-François Grollier, Paris; Jean Cotteret, Franconville; Andrée Bugaut, Boulogne; Alain Genet, Neuilly Plaisance, all of France

[73] Assignee: L'Oreal, Paris, France

[21] Appl. No.: 673,789

[22] Filed: Nov. 21, 1984

[30] Foreign Application Priority Data

Nov. 21, 1983 [LU] Luxembourg ............ 85098

[51] Int. Cl.⁴ .................. A61K 7/13; C09B 67/22; D06P 1/19
[52] U.S. Cl. .................. 8/410; 8/414; 8/415
[58] Field of Search .................. 8/415, 410

[56] References Cited

U.S. PATENT DOCUMENTS 3,168,442  2/1965  Brunner et al. .................. 564/414

FOREIGN PATENT DOCUMENTS 741334   11/1955  United Kingdom .
1061515   3/1967  United Kingdom .
1104970   3/1968  United Kingdom .
2112818   7/1983  United Kingdom .

OTHER PUBLICATIONS

J. F. Corbett in Venkataraman's "The Chemistry of Synthetic Dyes", vol. V, (Academic Press, 1971), pp. 507–514.

Primary Examiner—A. Lionel Clingman
Attorney, Agent, or Firm—Cushman, Darby & Cushman

[57] ABSTRACT

The invention provides a composition and process for directly dyeing keratinic fibres. The combination of 1-N-methylamino-2-nitro-4-N'-methyl-N'-(2',3'-dihydroxypropyl)amino benzene with certain 2-nitro-paraphenylenediamine direct nitro dyes produces a dye composition in which the dyes can be more concentrated (without crystallizing out) and hence produce darker shades.

21 Claims, No Drawings

Microfiche Appendix Included
(04181986 Microfiche, Clingman; A. Lionel Pages)

DYE COMPOSITION FOR THE DIRECT DYEING OF KERATINIC FIBRES, CONTAINING AT LEAST ONE N-SUBSTITUTED COSOLUBILIZED 2-NITROPARAPHENYLENEDIAMINE AND CORRESPONDING PROCESSES FOR DYEING KERATINIC FIBRES

The present invention relates to a dye composition for the direct dyeing of keratinic fibres, and, in particular, human hair. This composition contains at least one direct nitro dye which is an N-substituted 2-nitroparaphenylenediamine. The invention also relates to dyeing processes using the composition.

It is known to use nitroparaphenylenediamines and their substitution products in the composition of dye solutions for dyeing keratinic fibres, both in so-called oxidation dyeing and in direct dyeing, also known as semipermanent dyeing. However, oxidation dyes cannot always be tolerated, in particular by sensitive or damaged hair, because of the concentration of alkalizing agent and the presence of oxidizing agent. This may result in a preference for direct dyeing which is less sensitizing and less toxic owing to the absence of oxidizing agent and the much more moderate quantity of alkalizing agent.

In direct hair dyeing, blue and violet shades are necessary to produce the shades of natural appearance. It has been proposed to use as blue or violet direct hair dyes derivatives of 2-nitroparaphenylenediamine in which the amino group in the 4-position is disubstituted and the amino group in the 1-position is capable of being monosubstituted.

However, these conventional derivatives of 2-nitroparaphenylenediamine are in most cases inadequately soluble or dispersible in water, which represents a major disadvantage in producing dark and natural shades. When the dye is not adequately dissolved or dispersed in the medium dye irregularities result, with a high risk of producing colors which are weaker than those intended. In fact, when dye formulations which are rich in dyes for obtaining varied shades or carriers which only poorly solubilise the dye are used, the dyes recrystallize, remain in the dye bath and are not transferred to the hair.

The dye compositions produced from these 2-nitroparaphenylenediamine derivatives whose amino group in the 4-position is disubstituted and whose amino group in the 1-position may optionally be monosubstituted, have not, therefore, wholly satisfied hitherto the requirements for good dyeing.

We have discovered that by introducing 1-N-methylamino-2-nitro-4-N'-methyl-N'-(2',3'-dihydroxypropyl)-aminobenzene and/or at least one of its acid salts into a dyeing composition containing at least one blue or violet direct nitro dye consisting of a 2-nitroparaphenylenediamine whose amino group in the 4-position is disubstituted by alkyl or monohydroxyalkyl groups, and whose amino group in the 1-position is optionally monosubstituted by alkyl or monohydroxyalkyl groups, the solubility of the blue or violet direct nitro dye(s) is improved by a cosolubilization phenomenon.

The dye compositions according to the invention offer the advantage of dyeing hair, using the highly advantageous method of direct dyeing, to shades which can be very intense and very deep. Moreover, it is possible to exploit better the potential dyeing power of the 2-nitroparaphenylenediamine direct nitro dye substituted as indicated above. In fact, since 1-N-methylamino-2-nitro-4-N'-methyl-N'-(2',3'-dihydroxypropyl)aminobenzene is itself a violet dye, it is possible to obtain darker shades than with the poorly soluble 2-nitroparaphenylenediamine derivatives alone. Furthermore, the cosolubilizing agent introduced makes it possible to avoid the risk of recrystallization of the direct nitro dyes of the 2-nitroparaphenylenediamine series in those dye formulations which are rich in these dyes or which contain a poorly solubilizing carrier.

The present invention provides a dye composition for direct dyeing of keratinic fibres and, more particularly, human hair, containing, in a suitable vehicle, at least one direct nitro dye of formula:

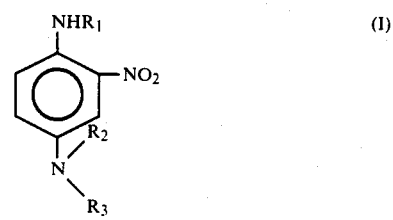

in which $R_1$ is hydrogen, an alkyl group of 1 to 4 carbon atoms or a monohydroxyalkyl group of 2 to 4 carbon atoms; $R_2$ is a monohydroxyalkyl group of 2 to 4 carbon atoms; and $R_3$ is an alkyl group of 1 to 4 carbon atoms or a monohydroxyalkyl group of 2 to 4 carbon atoms, or salt thereof, which composition also contains a compound of the formula:

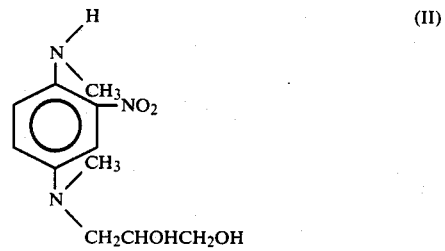

or inorganic or organic acid salt thereof.

Among the salts of the compound of formula (II), monohydrochloride may be mentioned as an example.

The compounds of formula (I) whose solubility can be increased by virtue of the presence of the compound of formula (II) are particularly those in which $R_1$ denotes a methyl group, and $R_2$ and $R_3$ each denote a β-hydroxyethyl group; or $R_1$ and $R_3$ each denote a methyl group and $R_2$ denotes a β-hydroxyethyl group; or $R_1$, $R_2$ and $R_3$ each denote a β-hydroxyethyl group; or $R_1$ and $R_2$ each denote a β-hydroxyethyl group, and $R_3$ denotes a methyl group; and the corresponding acid salts.

The following table collates the solubility limits at 18° C. of the four dyes of formula (I) referred to above, in the presence of increasing quantities y of the dye of formula (II), these solubility limits being measured in the following composition:

| | |
|---|---|
| monohydrochloride of the dye of formula (II) | y g |
| dye of formula (I) | x g |
| ethylene glycol monoethyl ether | 10 g |
| 2-amino-2-methyl-1-propanol q.s. | pH 9.6 |

| | -continued | |
|---|---|---|
| water q.s. | | 100 g | x is the maximum quantity of the dye in question of formula (I) which may be dissolved in the particular carrier defined above. To determine the solubilities, the following procedure is followed:

A large excess of dye of formula (I) is dispersed with y g of the dye of formula (II) in the form of its hydrochloride, in the cosmetic base described above. The composition is left for 15 minutes at 60° C. (water bath) and cooled with ambient air with stirring for 30 minutes (it being ensured that the ambient temperature is above 18° C.). At the end of these 30 minutes, the composition is introduced into an enclosure maintained at 18° C. The composition must remain therein for at least 48 hours. After being removed from the enclosure, the composition is immediately filtered. The filtrates collected are then analysed by HPLC to determine the dye content.

| | Solubility limits of the dye of formula (I) | | | |
|---|---|---|---|---|
| | Alone | Combined with the dye of formula (II) | | |
| Dye of formula (I) | y = 0 | y = 0.5 g | y = 1 g | y = 1.5 g |
| H–N(CH₃)–φ(NO₂)–N(CH₃)(CH₂CH₂OH) | 0.07% | 0.20% (2.85)* | 0.26% (3.71) | 0.35% (5) |
| H–N(CH₃)–φ(NO₂)–N(CH₂CH₂OH)(CH₂CH₂OH) | 0.32% | 0.57% (1.78) | 0.87% (2.71) | 1.12% (3.5) |
| H–N(CH₂CH₂OH)–φ(NO₂)–N(CH₃)(CH₂CH₂OH) | 0.36% | 0.46% (1.27) | 0.62% (1.72) | 0.74% (2.05) |
| H–N(CH₂CH₂OH)–φ(NO₂)–N(CH₂CH₂OH)(CH₂CH₂OH) | 0.74% | 1.00% (1.35) | 1.26% (1.70) | 1.57% (2.12) |

*The figure shown in brackets shows the improvement in the solubility of the dye of formula (I) in the presence of the dye of formula (II). Thus, the dye of formula (I) mentionaed first is 2.85 times more soluble in the abovementioned carrier when the quantity of the compound of formula (II) in the said carrier changes from 0 to 0.5 g.

The compounds of formula (I) are in particular described in French Pat. Nos. 1,101,904, 1,411,124, 1,454,313, 1,454,314, and in U.S. Pat. No. 3,168,442.

The compound of formula (II) can be obtained by reacting glycidol with the known compound of formula (III):

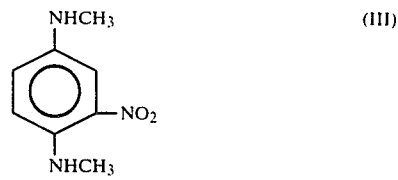

The compound of formula (III) may be obtained from 1-methylamino-2-nitro-4-aminobenzene, as described inter alia, in Example 2 of U.S. Pat. No. 3,274,249.

In accordance with preferred embodiments of the invention, the compound of formula (I) (or salt thereof) is present in the dye composition at a concentration of from 0.05% to 5% by weight and, in particular, from 0.1 to 3% by weight, expressed as free base, relative to the total weight of the composition; the compound of formula (II) (or salt thereof) is present in the composition at a concentration of from 0.1% to 5% by weight and, preferably, from 0.3% to 3% by weight, expressed as free base, relative to the total weight of the composition.

In addition to the compounds of formula (I) and (II) in the free state or in the form of salt, the dye compositions may incorporate direct nitro dyes other than those of formula (I) and (II), or direct non-nitro dyes such as, for example, azo dyes, anthraquinone dyes and naphthoquinone dyes.

The dye compositions may incorporate, as a suitable vehicle, water and/or cosmetically acceptable organic solvents and, more particularly, alcohols such as ethyl alcohol, isopropyl alcohol and benzyl alcohol, phenylethyl alcohol or glycols or glycol ethers such as, for example, ethylene glycol and its monomethyl, monoethyl and monobutyl ethers, propylene glycol, butylene glycol, dipropylene glycol, and diethylene glycol alkyl ethers such as, for example, diethylene glycol monoethyl ether or monobutyl ether, in concentrations of from 0.5 to 20% and, preferably, from 2 to 10% by weight relative to the total weight of the composition.

It is also possible to add to the composition fatty amides such as the mono- and diethanolamides of lauric acid, oleic acid or acids derived from copra, in concentrations of from 0.05 to 10% by weight.

It is also possible to add to the composition anionic, cationic, nonionic, or amphoteric surface-active agents or their mixtures. Preferably, the surfactants are present in the composition in a proportion of from 0.1 to 50% by weight, and, advantageously, from 1 to 20% by weight relative to the total weight of the composition.

Preferred surface-active agents include anionic surface-active agents used alone or mixed, such as particularly alkali metal salts, magnesium salts, ammonium salts, amine salts and alkanolamine salts of the following compounds:

alkyl sulphates, alkyl ether sulphates, ethoxylated or non-ethoxylated alkylamide sulphates, alkylsulphonates, alkylamidesulphonates, alpha-olefinesulphonates;

alkylsulphoacetates, the alkyl radicals of these compounds having a straight chain with 12 to 18 carbon atoms.

It is also possible to use, in the form of the abovementioned salts, fatty acids such as lauric, myristic, oleic, ricinoleic, palmitic and stearic acids, copra oil acids, hydrogenated copra oil acids, and carboxylic acids of polyglycol ethers.

As cationic surface-active agents, mention can be made more particularly of salts of fatty amines, quaternary ammonium salts such as alkyldimethylbenzylammonium, alkyltrimethylammonium, alkyldimethylhydroxyethylammonium and dimethyldialkylammonium chlorides and bromides, alkylpyridinium salts, and imidazoline derivatives. The alkyl groups in the abovementioned quaternary ammonium derivatives are long-chain groups having, preferably, between 12 and 18 carbon atoms.

Mention can also be made of amine oxides among these compounds of cationic nature.

Among amphoteric surface-active agents which may be employed mention can be made particularly of: alkylamino(mono- and di)propionates, betaines such as alkylbetaines, N-alkylsulphobetaines, N-alkylaminobetaines, in which the alkyl radical contains from 1 to 22 carbon atoms, and cycloimidiniums.

Among the nonionic surfactants which may optionally be employed in the compositions according to the invention, mention can be made of: the condensation products of a monoalcohol, an alkylphenol, an amide, or an α-diol with glycidol, such as the compounds prepared according to French Pat. Nos. 2,091,516, 2,169,787 and 2,328,763; the compounds of formula:

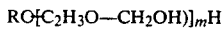

RO$\{C_2H_3O-CH_2OH)]_mH$ in which R denotes an alkyl, alkenyl or alkylaryl radical containing 8 to 22 carbon atoms and $1 \leq m \leq 10$; the polyethoxylated or polyglycerolated alcohols, alkylphenols or fatty acids containing a straight $C_8-C_{18}$ fatty chain; condensates of ethylene and propylene oxides with fatty alcohols; polyethoxylated fatty amides containing at least 5 moles of ethylene oxide and polyethoxylated fatty amines.

The thickening products which may be added to the composition are preferably sodium alginate, gum arabic, guar gum, a cellulose derivative such as methyl cellulose, hydroxyethyl cellulose, hydroxypropylmethyl cellulose, carboxymethyl cellulose sodium salt or an acrylic acid polymer; it is also possible to employ an inorganic thickening agent such as bentonite. These thickeners are employed alone or mixed and, preferably, are present in a proportion of from 0.5 to 5% by weight relative to the total weight of the composition and, advantageously, from 0.5 to 3% by weight.

The dye compositions according to the invention may be formulated at an acidic, neutral or alkaline pH, the pH generally being from 4 to 10.5 and, preferably, from 6 to 10. Among the alkalizing agents which may be employed mention can be made of alkanolamines, and alkali metal or ammonium hydroxides and carbonates. Among the acidifying agents which may be employed mention can be made of lactic acid, acetic acid, tartaric acid, phosphoric acid, hydrochloric acid and citric acid.

The dye compositions may additionally contain various conventional adjuvants such as antioxidants, perfumes, sequestering agents, film-forming agents, processing agents, dispersants, hair conditioners, preserving agents, opacifiers, and any other adjuvant usually employed in cosmetics.

The dye composition according to the invention may be in the various usual forms for dyeing hair, such as thickened or gelled liquids, creams, foams in aerosols or any other appropriate form for dyeing keratinic fibres.

The present invention also provides two new processes for dyeing keratinic fibres and in particular human hair. In accordance with the first process, the dye composition defined above is allowed to act on the dry or moist keratinic fibres for a time of application of from 3 to 60 minutes, preferably from 5 to 45 minutes, after which the keratinic fibres are rinsed, washed and rinsed again if appropriate and dried. In accordance with the second process, the compositions defined above are employed as nonrinsed lotions, that is to say that the compositions according to the invention are applied to the keratinic fibres and drying is then carried out without intermediate rinsing.

The dye compositions according to the invention may be applied to natural or dyed hair, which is or is not permanently waved, or to highly or slightly bleached and, if appropriate, permanently waved hair.

The following examples illustrate the invention.

EXAMPLE 1

The following dye composition is prepared:

| | |
|---|---|
| 1-N—Methylamino-2-nitro-4-N'—methyl-N'—(2',3'-Dihydroxypropyl)aminobenzene monohydrochloride | 1.5 g |
| 1-N—Methylamino-2-nitro-4-N',N'—bis-(β-hydroxyethyl)aminobenzene | 1.3 g |
| 1-N—(β-Hydroxyethyl)amino-2-methoxy-4-nitrobenzene | 0.2 g |
| (3-N—Methylamino-4-nitro)phenoxyethanol | 0.1 g |
| (3-N—Methylamino-4-nitro)phenyl,β,γ-dihydroxypropyl ether | 0.6 g |
| Lauryl diethanolamide | 2.5 g |
| Lauric acid | 1.5 g |
| Lauryl alcohol with 40 moles of ethylene oxide | 3 g |
| Ethylene glycol monoethyl ether | 5 g |
| Hydroxyethyl cellulose sold under the name "NATROSOL 250 HHR" by the Company "HERCULES" | 0.1 g |
| 2-Amino-2-methyl-1-propanol q.s. | pH 9.5 |
| Water q.s. | 100 g |

Thirty minutes' application of this composition to natural hair which is dark but of irregular color produces, when rinsing and drying is carried out, a natural, uniform brown shade.

EXAMPLE 2

The following dye composition is prepared:

| | |
|---|---|
| 1-N—Methylamino-2-nitro-4-N'—methyl-N'—(2',3'-dihydroxypropyl)aminobenzene monohydrochloride | 0.9 g |
| 1-N—Methylamino-2-nitro-4-N'—methyl-N'—(β-hydroxyethyl)aminobenzene | 0.4 g |
| "Disperse Black 9" sold under the name of "Noir diazo acetoquinone BSNZ 1350" by the Company "PCUK" | 0.1 g |
| 3-Nitro-4-N—(β-hydroxyethyl)aminophenol | 0.01 g |
| 3-Nitro-4-aminophenol | 0.1 g |
| 1-N—(β-hydroxyethyl)-2-methoxy-4-nitrobenzene | 0.1 g |
| (3-N—Methylamino-4-nitro)phenoxyethanol | 0.1 g |
| Nonylphenol oxyethylenated with 9 moles of ethylene oxide | 8 g |
| Oleyl diethanolamide | 2 g |
| Ethylene glycol monobutyl ether | 10 g |
| Hydroxypropyl cellulose sold under the name | 0.15 g |

-continued

| | |
|---|---|
| "KLUCEL G" by the Company "HERCULES" | |
| Monoethanolamine q.s. | pH 9.5 |
| Demineralized water q.s. | 100 g |

This liquid composition is applied for 30 minutes to light chestnut hair. The hair is rinsed and dried. A golden light chestnut color with irridescent gleams is obtained.

EXAMPLE 3

The following dye composition is prepared:

| | |
|---|---|
| 1-N—Methylamino-2-nitro-4-N'—methyl-N'—(2',3'-dihydroxypropyl)aminobenzene monohydrochloride | 1.1 g |
| 1-N—(β-hydroxyethyl)amino-2-nitro-4-N',N'—bis-(β-hydroxyethyl)aminobenzene | 0.65 g |
| "Disperse Blue 1" sold under the name "BLEU CELLITON EXTRA" by the Company "BASF" | 0.1 g |
| "Disperse Black 9" sold under the name "NOIR DIAZO ACETOQUINONE BSNZ 1350" by the Company "PCUK" | 0.1 g |
| (3-N—Methylamino-4-nitro)phenoxyethanol | 0.12 g |
| Lauryl diethanolamide | 2.5 g |
| Lauric acid | 1.5 g |
| Lauryl alcohol oxyethylenated with 40 moles of ethylene oxide | 3 g |
| Ethylene glycol monoethyl ether | 5 g |
| Hydroxyethyl cellulose sold under the name "NATROSOL 250 HHR" by the Company "HERCULES" | 0.1 g |
| 2-Amino-2-methyl-1-propanol q.s. | pH 9.5 |
| Demineralized water q.s. | 100 g |

This composition is applied for 30 minutes to natural, sun-bleached dark chestnut hair which has a small percentage of grey hair. After being rinsed and dried, the hair has recovered its original color and the grey hair has been shaded out.

EXAMPLE 4

The following dye composition is prepared:

| | |
|---|---|
| 1-N—Methylamino-2-nitro-4-N'—methyl-N'—(2',3'-dihydroxypropyl)aminobenzene monohydrochloride | 0.7 g |
| 1-N—(β-Hydroxyethyl)-2-nitro-4-N'—methyl-N'—(β-hydroxyethyl)aminobenzene | 0.6 g |
| (3-N—Methylamino-4-nitro)phenoxyethanol | 0.10 g |
| 4-N—(β-Hydroxyethyl)amino-3-nitrophenoxyethanol | 0.5 g |
| 2-Amino-3-nitrophenol | 0.2 g |
| Nonylphenol oxyethylenated with 9 moles of ethylene oxide | 8 g |
| Oleyl diethanolamide | 2 g |
| Ethylene glycol monobutyl ether | 10 g |
| Hydroxypropyl cellulose sold under the name "KLUCEL G" by the Company "HERCULES" | 0.15 g |
| Monoethanolamide q.s. | pH 9.5 |
| Demineralized water q.s. | 100 g |

This liquid composition is applied to light chestnut hair for 30 minutes. After being rinsed and dried the hair has a purple-violet mahogany-colored sheen.

EXAMPLE 5

The following dye composition is prepared:

| | |
|---|---|
| 1-N—Methylamino-2-nitro-4-N'—methyl-N'—(2',3'-dihydroxypropyl)aminobenzene monohydrochloride | 1.0 g |
| 1-N—(β-Hydroxyethyl)amino-2-nitro-4-N',N'—bis-(β-hydroxyethyl)aminobenzene | 0.4 g |
| 1-N—(β-Hydroxyethyl)amino-2-nitro-4-N'—methyl-N'—(β-hydroxyethyl)aminobenzene | 0.3 g |

-continued

| | |
|---|---|
| 1-Amino-2-nitro-5-methyl-4-N—(β-hydroxyethyl)aminobenzene | 0.05 g |
| 1-Amino-2-nitro-4-N—(β-hydroxyethyl)aminobenzene | 0.1 g |
| 2-N—(β-Hydroxyethyl)amino-5-nitrophenol | 0.3 g |
| 1-Amino-2-nitro-6-methylbenzene | 0.2 g |
| Lauryl diethanolamide | 4 g |
| Ammonium laurylsulphate sold under the name "SACTIPON 286" by the Company "LEVER" | 20 g |
| Mixture of methylchloroisothiazolinone and methylisothiazolinone sold under the name "KATHON CG" by the Company "ROHM & HAAS" | 0.05 g |
| Acrylic acid polymer with a molecular weight of 2 to 3 million, sold under the name "CARPOBOL 934" by the Company "GOODRICH CHEMICAL Co" | 0.5 g |
| Ethylene glycol monoethyl ether | 4 g |
| 2-Amino-2-methyl-1-propanol q.s. | pH 9 |
| Demineralized water q.s. | 100 g |

This composition is applied to chestnut hair. After 30 minutes' application the hair is rinsed and dried. The hair is then colored with a golden chestnut shade.

EXAMPLE 6

The following dye composition is prepared:

| | |
|---|---|
| 1-N—(β-Hydroxyethyl)amino-2-nitro-4-N,N'—bis-(β-hydroxyethyl)aminobenzene | 2 g |
| 1-N—Methylamino-2-nitro-4-N'—methyl-N'—(2',3'-dihydroxypropyl)aminobenzene monohydrochloride | 2 g |
| 1-N—(β-Hydroxyethyl)amino-2-methoxy-4-nitrobenzene | 0.05 g |
| (3-N—Methylamino-4-nitro)phenoxyethanol | 0.1 g |
| (3-N—Methylamino-4-nitro)phenyl,β,γ-dihydroxypropyl ether | 0.53 g |
| "Disperse Black 9" sold under the name "NOIR DIAZO ACETOQUINONE BSNZ 1350" by the Company "PCUK" | 0.2 g |
| "Disperse Blue 1" sold under the name "BLEU CELLITON EXTRA" by the Company "BASF" | 0.1 g |
| Lauric acid | 1 g |
| Lauryl diethanolamide | 2 g |
| Tallow amide polyoxyethylenated with 50 moles of ethylene oxide sold under the name "ETHOMID HT 60" by the Company "AKZO" | 3 g |
| Ethylene glycol monobutyl ether | 4.5 g |
| Hydroxyethyl cellulose sold under the name "CELLOSIZE WP03H" by the Company "UNION CARBIDE" | 3.5 g |
| Monoethanolamide q.s. | pH 9.6 |
| Demineralized water q.s. | 100 g |

This composition is applied for 30 minutes to brown hair. After rinsing and drying, a dark ash brown shade is produced in this hair.

EXAMPLE 7

The following dye composition is prepared:

| | |
|---|---|
| 1-N—(β-Hydroxyethyl)amino-2-nitro-4-N',N'—bis-(β-hydroxyethyl)aminobenzene | 2 g |
| 1-N—Methylamino-2-nitro-4-N'—methyl-N'—(2',3'-dihydroxypropyl)aminobenzene monohydrochloride | 2 g |
| 5-Hydroxy-2-amino-1-nitrobenzene | 0.2 g |
| 3-Hydroxy-2-amino-1-nitrobenzene | 1 g |
| (3-N—methylamino-4-nitro)phenyl,β,γ-dihydroxypropyl ether | 0.9 g |
| (3-N—Methylamino-4-nitro)phenoxyethanol | 0.1 g |
| 1-N—(β-Hydroxyethyl)amino-2-methoxy-4-nitrobenzene | 0.1 g |
| "Disperse Black 9" sold under the name "NOIR DIAZO ACETOQUINONE BSNZ 1350" by the Company "PCUK" | 0.2 g |
| "Disperse Blue 1" sold under the name "BLEU CELLITON EXTRA" by the Company "BASF" | 0.1 g |
| Lauric acid | 1 g |

-continued

| | |
|---|---|
| Lauryl diethanolamide | 2 g |
| Tallow amide polyoxyethylenated with 50 moles of ethylene oxide sold under the name "ETHOMID HT 60"by the Company "AKZO" | 3 g |
| Ethylene glycol monobutyl ether | 4.5 g |
| Hydroxyethyl cellulose sold under the name "CELLOSIZE WP03H" by the Company "UNION CARBIDE" | 3.5 g |
| Monoethanolamine q.s. | pH 9.6 |
| Demineralized water q.s. | 100 g |

This composition is applied for 30 minutes to brown hair. After rinsing and drying, hair of a strong golden brown color is obtained.

We claim:

1. A dye composition for use in the direct dyeing of keratinic fibers comprising, in a suitable vehicle, (a) a keratinic fiber-dyeing amount of at least one direct nitro dye of the formula

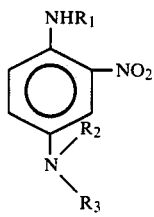

wherein $R_1$ is hydrogen, alkyl having 1-4 carbon atoms or monohydroxy alkyl wherein the alkyl moiety has 2-4 carbon atoms, $R_2$ is monohydroxy alkyl wherein the alkyl moiety has 2-4 carbon atoms, $R_3$ is alkyl having 1-4 carbon atoms or monohydroxy alkyl wherein the alkyl moiety has 2-4 carbon atoms, or a salt thereof, and (b) an amount effective to increase the solubility of said direct nitro dye of (a), above, in said vehicle, of a compound of the formula

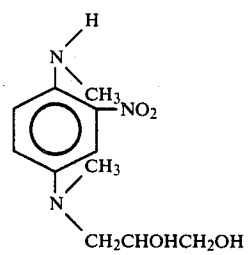

or a salt thereof.

2. A composition according to claim 1, wherein in formula (I) $R_1$ is a methyl group, and $R_2$ and $R_3$ are each a β-hydroxyethyl group.

3. A composition according to claim 1, wherein in formula (I) $R_1$ and $R_3$ are each a methyl group, and $R_2$ is a β-hydroxyethyl group.

4. A composition according to claim 1, wherein in formula (I) $R_1$, $R_2$ and $R_3$ are each a β-hydroxyethyl group.

5. A composition according to claim 1, wherein in formula (I) $R_1$ and $R_2$ are each a β-hydroxyethyl group, and $R_3$ is a methyl group.

6. A composition according to claim 1, in which the compound of formula (I) or salt thereof, is present in the composition at a concentration of from 0.05% to 5% by weight, expressed as free base, relative to the total weight of the composition.

7. A composition according to claim 6, in which the compound of formula (I) or salt thereof, is present in the composition at a concentration of from 0.1 to 3% by weight.

8. A composition according to claim 1, in which the compound of formula (II) or salt thereof, is present in the composition at a concentration of from 0.1% to 5% by weight, expressed as free base, relative to the total weight of the composition.

9. A composition according to claim 8, in which the compound for formula (II) is present in the composition at a concentration of from 0.3% to 3% by weight.

10. A composition according to claim 1, which contains at least one direct nitro dye other than those of formulae (I) and (II).

11. A composition according to claim 1, which contains at least one direct non-nitro dye.

12. A composition according to claim 11, in which the non-nitro dye is an azo dye, naphthoquinone dye or anthraquinone dye.

13. The composition of claim 1 wherein said vehicle is water, an organic solvent or a mixture thereof, said organic solvent being present in an amount of from 0.5 to 20% by weight relative to the total weight of said composition.

14. A composition according to claim 1, which contains from 0.1 to 50% by weight, relative to the total weight of the composition, of at least one surface-active agent.

15. A composition according to claim 1, which contains at least one thickening agent present in a concentration of from 0.5 to 5% by weight relative to the total weight of the composition.

16. A composition according to claim 1, which additionally contains as adjuvant, one or more antioxidant, alkalizing or acidifying agent, perfume, sequestering agent, film-forming agent, processing agent, dispersant, hair conditioner, preserving agent, or opacifier.

17. A composition according to claim 1, which has a pH of from 4 to 10.5.

18. A composition according to claim 17, in which the pH is from 6 to 10.

19. A composition according to claim 1, which is in the form of a thickened or gelled liquid, cream, or aerosol foam.

20. A process for dyeing keratinic fibres, in which a composition according to claim 1 is allowed to act on dry or moist keratinic fibres for from 3 to 60 minutes, and then the keratinic fibres are rinsed, washed and rinsed again if appropriate, and dried.

21. A process for dyeing keratinic fibres, in which a composition according to claim 1 is applied to keratinic fibres, followed by drying without intermediate rinsing.

* * * * *